(12) United States Patent
Perez-Cruet et al.

(10) Patent No.: US 7,407,483 B2
(45) Date of Patent: Aug. 5, 2008

(54) MINIMALLY INVASIVE SURGICAL ACCESS DEVICE

(76) Inventors: Mick J. Perez-Cruet, 1070 Timberlake Dr., Bloomfield, MI (US) 48302; John R. Pepper, 224 Beacon Hill Dr., Cheshire, CT (US) 06410

( * ) Notice: Subject to any disclaimer, the term of this patent is extended or adjusted under 35 U.S.C. 154(b) by 182 days.

(21) Appl. No.: 11/377,466

(22) Filed: Mar. 16, 2006

(65) Prior Publication Data

US 2007/0219416 A1   Sep. 20, 2007

(51) Int. Cl.
*A61B 1/32* (2006.01)
(52) U.S. Cl. ............... 600/219; 600/104; 600/185; 600/201; 600/233
(58) Field of Classification Search ............. 600/104, 600/184, 185, 201, 213, 219, 220, 222, 224, 600/232, 231, 233
See application file for complete search history.

(56) References Cited

U.S. PATENT DOCUMENTS

| | | | | |
|---|---|---|---|---|
| 400,589 A | * | 4/1889 | Molesworth | ............... 600/203 |
| 4,690,132 A | * | 9/1987 | Bayer et al. | ............... 600/219 |
| 5,489,210 A | * | 2/1996 | Hanosh | ............... 433/173 |
| 6,007,337 A | * | 12/1999 | Bauer | ............... 433/173 |
| 6,364,832 B1 | * | 4/2002 | Propp | ............... 600/220 |
| 6,451,057 B1 | * | 9/2002 | Chen et al. | ............... 623/17.15 |

* cited by examiner

*Primary Examiner*—Hao D Mai
(74) *Attorney, Agent, or Firm*—John A. Miller, Esq.; Miller IP Group, PLC

(57) ABSTRACT

A minimally invasive surgical access device that allows access to a pathology being treated while significantly reducing the risk of damaging anatomical structures proximate the pathology. The access device includes a base portion having a central bore extending therethrough, and retractor blades pivotably mounted to the base portion. An insertion handle is coupled to the base portion to thread the retractor blades into the patient. The insertion handle is removed from the base portion, and a core hollow screw is threaded into the base portion to separate the retractor blades to gain access to the pathology through the hollow screw.

22 Claims, 4 Drawing Sheets

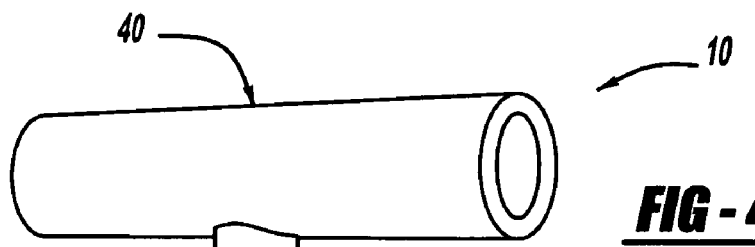
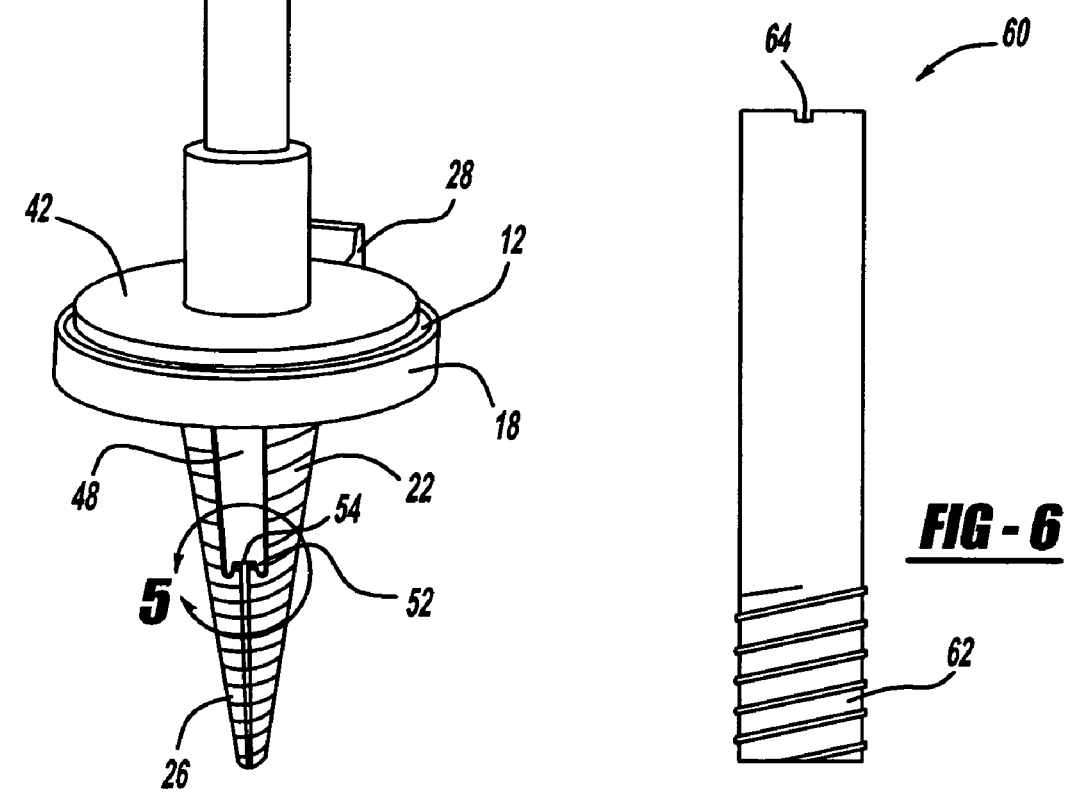
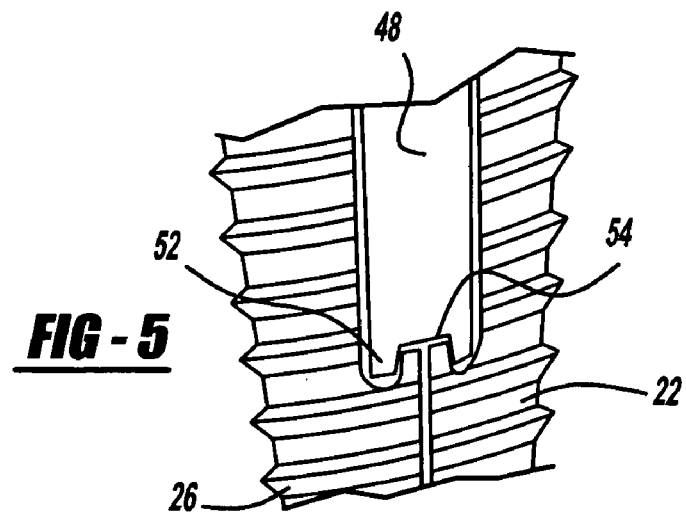

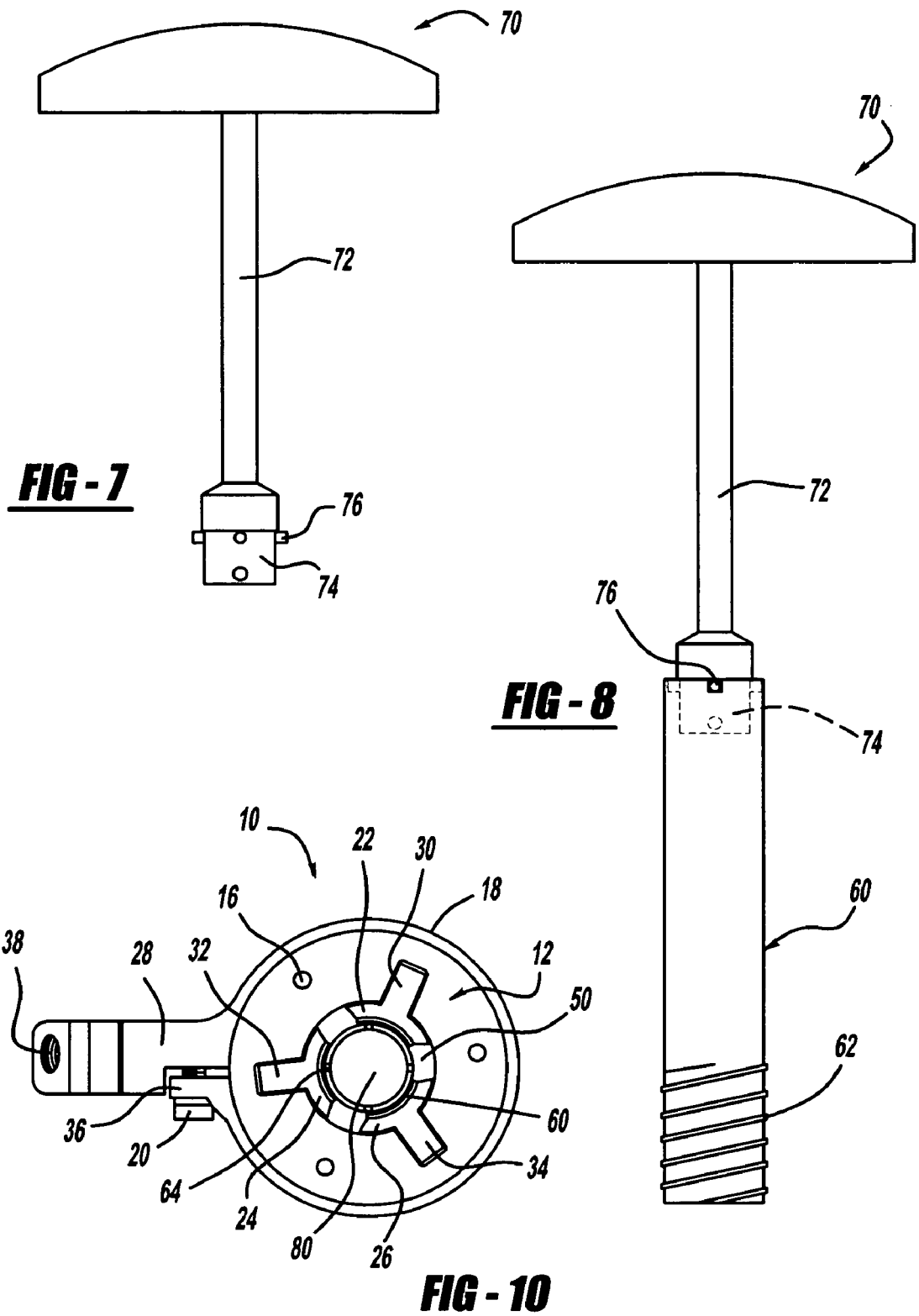

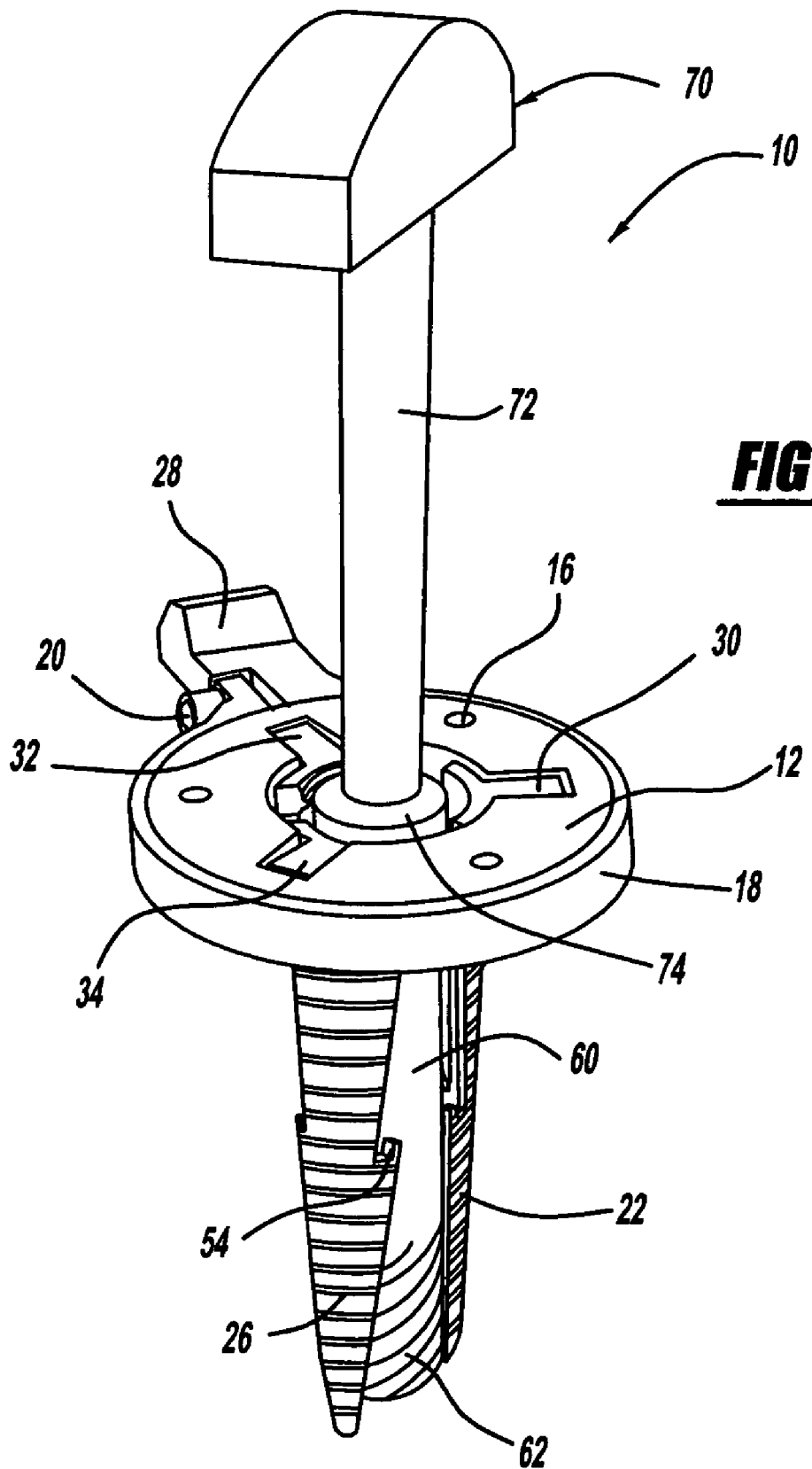

MINIMALLY INVASIVE SURGICAL ACCESS DEVICE

BACKGROUND OF THE INVENTION

1. Field of the Invention

This invention relates generally to a minimally invasive access device for a surgical procedure and, more particularly, to a minimally invasive access device for spinal surgery, where the device includes retractor blades and an access tube, where the access tube is threaded into the retractor blades to cause them to separate, which provides a corridor for accessing a surgical pathology.

2. Discussion of the Related Art

Traditional surgical approaches for the human body involve the dissection of supporting structures, such as muscle, ligaments and/or bone, to access and expose the pathology being treated. These structures are usually vital to the long term health and function of the body. Typically, these structures are not involved in a disease process, but frequently need to be removed or dissected in order to gain visualization of the pathology.

In the case of spinal disorders, the supporting muscle and ligaments of the spine are removed to expose the underlying bony part of the spine where the pathology is typically located. These supporting structures are not causing the patient any discomfort or pain, however, because the surgeon must be able to visualize the surgical operation, they need to be removed or detached. For example, in the treatment of a lumbar disk herniation or stenosis, the muscle and ligaments are dissected from the spine to expose the lamina of the spine, sometimes over many levels of the spine. In performing spinal fusion and instrumentation, extensive muscle and ligamentous detachment may be performed. As a result, these tissues never return to their normal anatomical position, which is disrupted in the surgical process, weakening their function and strength. Also, the patient may experience significant pain and discomfort resulting in longer hospital stays and recoveries. The long term health of the spine can also be affected because these supporting structures are not able to perform their function normally. This can result in further pain and discomfort, and can even lead to additional surgeries.

A frequently encountered problem is transitional syndrome whereby the nerves adjacent to an open fusion and instrumentation become compressed. The treatment is often an additional surgery with extension of the fusion and instrumentation. This may in-part be due to the initial fusion procedure dissecting supporting muscles and ligaments creating an iatrogenic instability that leads to adjacent level stenosis. In addition, large open procedures often result in extensive scar formation that can lead to conditions such as arachnoiditis and failed back syndrome. These patients suffer significant and debilitating pain which is often refractory to additional surgery. Many can no longer work or conduct normal activities of daily living.

In an attempt to preserve normal anatomical structures during spine surgery, minimally invasive surgical procedures have been devised. One such procedure involves the use of a series of muscle dilators that spread open the muscle fibers of the spine to create a pathway to the spine. A Kirschner (K) wire (a thin metal wire) is initially introduced through a small incision and directed towards the spinal pathology. The position of the K-wire is visualized by a fluoroscopic imaging system to identify its location. An initial narrow diameter muscle dilator is passed over the K-wire, and the K-wire is removed and subsequent larger muscle dilators are continually passed. When the opening is large enough, an access tube or retractor is positioned around the last muscle dilator through which the surgery is performed. The inner sequential muscle dilators are then removed allowing the surgeon to operate through the tubular retractor. The retractors come in a variety of lengths and diameters for different patients and procedures.

Unfortunately, a number of complications have occurred using the previously described system. The K-wire is very thin and sharp and can be easily passed to deep and into the spinal cord or injure a nerve root or large blood vessel. Additionally considerable downward force is required to pass the muscle dilators towards the spine. Incidences have occurred in which the dilators are passed into the spinal canal resulting in neural injury and paralysis. The muscle dilators also tend to be pushed upward out of the wound requiring multiple repositioning during placement, each time placing the neural structures at risk. This is especially true for large muscular individuals. Lastly, multiple, sequentially larger dilators are used causing considerable patient risk with placement of each muscle dilator. Therefore, it is desirable to improve the known minimally invasive surgical access devices.

SUMMARY OF THE INVENTION

In accordance with the teachings of the present invention, a minimally invasive surgical access device is disclosed that allows access to a pathology being treated while significantly reducing the risk of damaging anatomical structures proximate the pathology. The access device includes a base portion having a bore extending therethrough. Retractor blades including inner and outer threads are pivotably mounted to the base portion. An insertion handle having an elongated body is attached to and extends through the bore in the base portion, and includes tabs for holding the retractor blades together in a conical orientation. The insertion handle is used to thread the retractor blades into the soft tissue of the patient towards the pathology. When the retractor blades are in place, the insertion handle is removed from the base portion, and a core hollow screw having a threaded outer portion is inserted through the opening of the base portion. An access handle is attached to the core hollow screw and is used to rotate the core hollow screw so that the threaded portion of the core hollow screw and the internal threads of the retractor blades interact to separate the retractor blades and expose the pathology through an internal bore in the core hollow screw.

Additional features of the present invention will become apparent from the following description and appended claims, taken in conjunction with the accompanying drawings.

BRIEF DESCRIPTION OF THE DRAWING

FIG. 4 is a perspective view of the insertion handle mounted to the base portion of the access device assembly;

FIG. 5 is an enlarged view of a portion of the retractor blades of the base portion showing how the retractor blades are locked together when the insertion handle is mounted to the base portion;

FIG. 6 is a front view of a core hollow screw that is threadably engagable with the retractor blades of the base portion;

FIG. 7 is a front view of an access handle that attaches to the core hollow screw to threadably insert the core hollow screw into the base portion;

FIG. 8 is a front view of the access handle attached to the core hollow screw;

FIG. 9 is a perspective view of the core hollow screw threaded into the retractor blades to expose the pathology being treated; and FIG. 10 is a top view of the base portion with the core hollow screw inserted into the retractor blades.

DETAILED DESCRIPTION OF THE EMBODIMENTS

The following discussion of the embodiments of the invention directed to a minimally invasive surgical access device is merely exemplary in nature, and is in no way intended to limit the invention or its applications or uses. For example, the access device of the invention has particular application for minimally invasive spinal surgical procedures. However, as will be appreciated by those skilled in the art, the access device of the invention will have application for other types of minimally invasive surgeries.

FIGS. 1-10 show various views of various components of a minimally invasive surgical access device assembly 10, according to an embodiment of the present invention. The various components of the assembly 10 can be fabricated and assembled by any suitable technique, such as molding, stamping, welding, etc., and can be made of any suitable material, such as aluminum, steel, radio-lucent carbon/graphite composites, etc.

Figure 1:
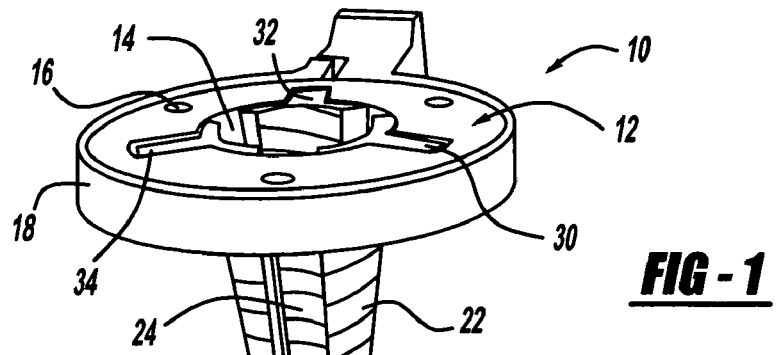
FIG. 1 is a perspective view of a base portion including pivotable retractor blades of a surgical access device assembly, according to an embodiment of the present invention.
Figure 2:
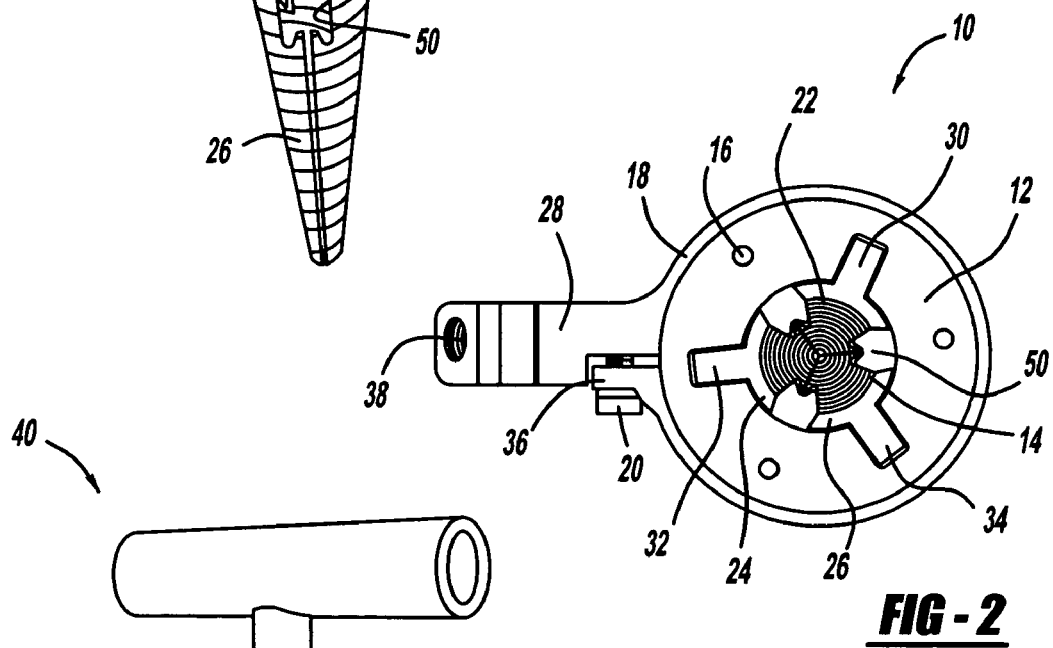
FIG. 2 is a top view of the base portion shown in FIG. 1.

As shown in FIGS. 1 and 2, the access device assembly 10 includes a round base portion 12 having a central bore 14 extending therethrough. Three small holes 16 are symmetrically disposed around the central bore 14 and also extend through the base portion 12. A mounting ring 18 is positioned around an outer edge of the base portion 12, and is clamped thereto by a bolt 20. The mounting ring 18 includes an extended portion 28, where the bolt 20 is threaded through a tab 36 across a gap into the extended portion 28 to rigidly mount the mounting ring 18 to the base portion 12. The extended portion 28 includes a threaded opening 38 that accepts a securing bolt of a holding arm (not shown). As would be well understood to those skilled in the art and more apparent from the discussion below, when the access device assembly 10 is being used in a surgical procedure, it needs to be rigidly mounted to a supporting structure, such as the operating table.

Three symmetrical retractor blades 22, 24 and 26 are pivotably mounted to the base portion 12. The retractor blade 22 includes an upper tab 30, the retractor blade 24 includes an upper tab 32 and the retractor blade 26 includes an upper tab 34. The tabs 30, 32 and 34 each have a bore extending therethrough. The base portion 12 includes a rod (not shown) extending across an opening in the base portion 12 in which each of the tabs 30, 32 and 34 is positioned. Thus, the retractor blades 22-26 are free to pivot on their independent rods. The retractor blades 22-26 have an inner thread and an outer thread for reasons that will become apparent from the discussion below. The internal and external threads of the retractor blades 22-26 need not be continuous between the blades 22-26, but can be in other embodiments. Further, when the retractor blades 22-26 are in their unpivoted position, the retractor blades 22-26 form a conical shape having a pointed end opposite to the base portion 12.

As will be appreciated by those skilled in the art, a conical shape for the retractor blades 22-26 is non-limiting in that the retractor blades 22-26 can form other shapes, such as a parabolic swept section, concave and convex orientations, stepped linear sections, a spiral, etc. Further, the cone can be unitary or broken up into multiple components along its axis. Further, the cone shape can be a canculated cone to allow it to follow a K-wire to the pathology. In this embodiment, there are three retractor blades. However, it other embodiments there may be more retractor blades within the scope of the present invention.

Figure 3:
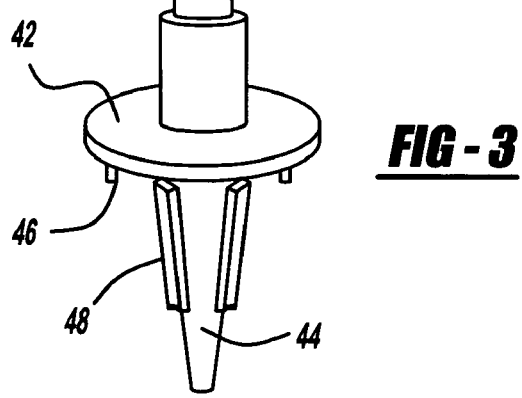
FIG. 3 is a perspective view of an insertion handle that attaches to the base portion of the access device assembly to thread the retractor blades through soft tissue of a patient.

As shown in FIG. 3, the access device assembly 10 also includes an insertion handle 40 having a support portion 42 and a conical bottom portion 44. In one embodiment, the insertion handle 40 can be a single piece unit made from a suitable material, such as aluminum. Three cylindrical pins 46 extend down from the support portion 42 and are configured to be inserted into the holes 16 in the base portion 12. Further, the conical portion 44 is dimensioned to fit within the retractor blades 22-26 when the retractor blades 22-26 are in their unpivoted position.

FIG. 4 is a perspective view of the insertion handle 40 attached to the base portion 12. The conical portion 44 includes three extending tabs 48 that are configured to be positioned within openings 50 between the retractor blades 22-26 at an upper location proximate the base portion 12. FIG. 5 is a blown-up view at this location of the assembly 10. The tabs 48 include a pair of fingers 52 that are inserted within notches 54 in two adjacent retractor blades 22-26 so that when the insertion handle 40 is positioned in the base portion 12, the retractor blades 22-26 are held in place and prevented from pivoting.

When the access handle 40 is positioned in the base portion 12, the pointed end of the retractor blades 22-26 are positioned over the pathology on the patient's skin. The handle 40 is rotated to thread the retractor blades 22-26 into the patient towards the pathology. The pins 46 in the support portion 42 prevent the handle 40 from being rotated relative to the base portion 12. Once the retractor blades 22-26 are fully inserted into the patient to the desired depth, the handle 40 can be removed from the base portion 12 by merely pulling up on it. The retractor blades 22-26 are unique in allowing for a single pass or access towards the spine, and once positioned and opened, to expose the spinal pathology while minimizing muscle or ligamentous resection. The screw type outer conical design allows for a controlled approach since the driving force to advance the retractor blades 22-26 toward the spine is a turning motion, not a downward forced motion. The rate of advancement of the tip of the retractor blades 22-26 is controlled at all times by the rate of rotation of the insertion handle 40. This significantly improves the safety of the assembly 10 for accessing the pathology.

FIG. 6 is a front view of a core hollow screw 60 that is part of the assembly 10. The core hollow screw 60 includes an outer threaded portion 62 at a bottom of the core hollow screw 60 that aligns with the inner threads of the retractor blades 22-26. A top edge of the core hollow screw 60 includes four symmetrically disposed cut-outs 64.

FIG. 7 is a front view of an access handle 70 including an elongated rod 72 and an end portion 74 having symmetrically disposed pins 76. FIG. 8 is a front view of the access handle 70 mounted to the core hollow screw 60 where the end portion 74 is positioned within an internal bore 80 of the core hollow screw 60 and the pins 76 are positioned within the cut-outs 64.

When the insertion handle 40 is removed from the base portion 12 after the retractor blades 22-26 are threaded into the patient, the surgeon will attach the access handle to the core hollow screw 60 and then position the threaded portion 62 of the core hollow screw 60 into the central bore 14 of the base portion 12. When the surgeon rotates the access handle 70 to turn the core hollow screw 60, the threaded portion 62 of the core hollow screw 60 and the retractor blades 22-26 interact to cause the core hollow screw 60 to be threaded downward, which causes the retractor blades 22-26 to pivot and separate.

FIG. 9 is a perspective view of the access device assembly 10, where the screw tube 60 has been threaded into the retractor blades 22-26. The distance that the core hollow screw 60 is inserted into the retractor blades 22-26 would depend on the surgical procedure being performed and the pathology being treated. Once the core hollow screw 60 is threaded into the retractor blades 22-26 to the proper distance, the handle 70 is removed from the core hollow screw 60, by pulling up on it. The internal bore 80 of the core hollow screw 60 is used to gain access to the pathology to perform the surgical procedure. FIG. 10 is a top view of the base portion 12 with the core hollow screw 60 in place showing the internal bore 80 through which the surgical procedure is performed. Different size access device assemblies including different diameter and length core hollow screws can be provided for treating different pathologies.

The discussion of the access device assembly 10 above has particular application for minimally invasive spinal surgery where the retractor blades are threaded through the patient's tissue towards the pathology. In alternate embodiments, the retractor blades 22-26 can be self-drilling through facia, muscle and soft tissue. Further, the retractor blades 22-26 may be able to be drilled into bone or cartilage to provide for nail entry portals, cranial access ports, bone compaction to prepare an ACL tunnel, tendon repair tunnel preparation, suture anchor, etc. The bone cutting version could have a cutting flute instead of the external threads on the retractor blades 22-26.

The foregoing discussion discloses and describes merely exemplary embodiments of the present invention. One skilled in the art will readily recognize from such discussion and from the accompanying drawings and claims that various changes, modifications and variations can be made therein without departing from the spirit and scope of the invention as defined in the following claims.

What is claimed is:

1. A surgical access device assembly comprising:
   a base portion including a central bore;
   a plurality of retractor blades pivotably mounted to the base portion and including an internal threaded portion, said plurality of retractor blades combining to form a predetermined internal shape in a closed position having a pointed end opposite to the base portion, said plurality of retractor blades including an external threaded portion operable to be threaded into a patient; and
   a first handle having an elongated body and an end portion that conforms to the predetermined internal shape of the plurality of retractor blades when the retractor blades are in the closed position, said retractor blades including a locking structure for securing the retractor blades in the closed position, said handle being rotatable so that the retractor blades are rotatable.

2. The assembly according to claim 1 wherein the base portion includes a plurality of holes and the first handle includes a plurality of pins positionable within the holes to hold the first handle to the base portion as it is rotated.

3. The assembly according to claim 1 wherein each of the plurality of retractor blades includes an upper tab that is pivotably mounted to a rod positioned within an opening in the base portion.

4. The assembly according to claim 1 wherein the end portion of the first handle includes a plurality of symmetrically disposed tabs having extended fingers and each of the plurality of retractor blades includes a notch portion where the fingers of the tabs are positioned within the notch portion to form the locking structure.

5. The assembly according to claim 1 wherein the plurality of retractor blades is three or more retractor blades.

6. The assembly according to claim 1 wherein the predetermined internal shape is selected from the group consisting of conical shapes, a parabolic swept section, concave shapes, convex shapes, stepped linear sections and spirals.

7. The assembly according to claim 1 further comprising a core hollow screw having an external threaded portion, said core hollow screw being operable to be threaded into the predetermined internal shape formed by the plurality of retractor blades when the first handle is removed from the base portion to cause the plurality of retractor blades to separate.

8. The assembly according to claim 7 further comprising a second handle having an elongated body, said second handle being attachable and detachable to and from the core hollow screw to thread the core hollow screw into the plurality of retractor blades.

9. The assembly according to claim 8 wherein the second handle includes a plurality of symmetrically disposed pins and the core hollow screw includes a plurality of symmetrically disposed cut-outs at a top edge of the core hollow screw where the pins on the second handle are positioned within the cut-outs to secure the second handle to the core hollow screw.

10. The assembly according to claim 1 further comprising a mounting ring rigidly mounted to an outer surface of the base portion, said mounting ring including an extended portion that is adaptable to receive a mounting arm.

11. A surgical access device assembly comprising:
    a base portion including a central bore;
    a plurality of retractor blades pivotably mounted to the base portion and including an internal threaded portion, said plurality of retractor blades combining to form a predetermined internal shape in a closed position having a pointed end opposite to the base portion, said plurality of retractor blades including an external threaded portion operable to be threaded into a patient; and
    a core hollow screw having an internal bore and an external threaded portion, said core hollow screw being operable to be threaded into the predetermined internal shape formed by the plurality of retractor blades to cause the plurality of retractor blades to separate.

12. The assembly according to claim 11 wherein each of the plurality of retractor blades includes an upper tab that is pivotably mounted to a rod positioned within an opening in the base portion.

13. The assembly according to claim 11 wherein the plurality of retractor blades is three or more retractor blades.

14. The assembly according to claim 11 wherein the predetermined internal shape is selected from the group consisting of conical shapes, a parabolic swept section, concave shapes, convex shapes, stepped linear sections and spirals.

15. The assembly according to claim 11 further comprising a handle having an elongated body of various length, said handle being attachable and detachable to and from the core hollow screw to thread the core hollow screw into the plurality of retractor blades.

16. The assembly according to claim 15 wherein the handle includes a plurality of symmetrically disposed pins and the core hollow screw includes a plurality of symmetrically disposed cut-outs at a top edge of the core hollow screw where the pins on the handle are positioned within the cut-outs to secure the handle to the core hollow screw.

17. The assembly according to claim 11 further comprising a mounting ring rigidly mounted to an outer surface of the base portion, said mounting ring including an extended portion that is adaptable to receive a mounting arm.

18. A surgical access device assembly comprising:
- a circular base portion including a circular central bore, said base portion further including a plurality of symmetrically disposed holes around the central bore;
- a plurality of retractor blades pivotably mounted to the base portion and including an internal threaded portion and an external threaded portion, each of the plurality of retractor blades including an upper tab pivotally mounted on a rod mounted in an opening of the base portion, said plurality of retractor blades combining to form a conical shape in a closed position having a pointed end opposite to the base portion;
- a first handle including an elongated body and a conical end portion that conforms to the internal shape of the plurality of retractor blades when the retractor blades are in the closed position, said first handle further including a plurality of symmetrically disposed pins mounted to a central support portion of the first handle that align with the symmetrically disposed holes in the base portion so as to allow the base portion to be rotated by the first handle when the first handle is attached to the base portion, said conical end portion of the first handle including a plurality of tab portions that interlock within openings between the plurality of retractor blades for securing the retractor blades in the closed position;
- a core hollow screw having an internal bore and an external threaded portion; and
- a second handle having an elongated body and being attachable and detachable to and from the core hollow screw, said second handle being operable to thread the core hollow screw into the plurality of retractor blades when the first handle is removed from the base portion to cause the plurality of retractor blades to separate.

19. The assembly according to claim 18 wherein the plurality of retractor blades is three or more retractor blades.

20. The assembly according to claim 18 wherein the second handle includes a plurality of symmetrically disposed pins and the core hollow screw includes a plurality of symmetrically disposed cut-outs at a top edge of the core hollow screw where the pins on the second handle are positioned within the cut-outs to secure the second handle to the core hollow screw.

21. The assembly according to claim 18 further comprising a mounting ring rigidly mounted to an outer surface of the base portion, said mounting ring including an extended portion that is adaptable to receive a mounting arm.

22. The assembly according to claim 18 wherein the plurality of tab portions is three symmetrically disposed tab portions including extended fingers and wherein each of the plurality of retractor blades includes a notch portion in which the fingers of the tab portions are positioned within.

* * * * *